US011534494B2

(12) United States Patent
Dyrstad et al.

(10) Patent No.: US 11,534,494 B2
(45) Date of Patent: Dec. 27, 2022

(54) FORMULATION AND METHOD OF SYNTHESIS

(71) Applicant: GE Healthcare Limited, Buckinghamshire (GB)

(72) Inventors: Knut Richard Dyrstad, Oslo (NO); Torild Wickstrom, Oslo (NO); Thanushan Rajanayagam, Oslo (NO); Kristine Romoren, Oslo (NO); Olav Ryan, Kjelsas (NO)

(73) Assignee: GE HEALTHCARE LIMITED, Buckinghamshire (GB)

( * ) Notice: Subject to any disclaimer, the term of this patent is extended or adjusted under 35 U.S.C. 154(b) by 46 days.

(21) Appl. No.: 16/997,188

(22) Filed: Aug. 19, 2020

(65) Prior Publication Data

US 2021/0030878 A1    Feb. 4, 2021

Related U.S. Application Data (60) Continuation-in-part of application No. 15/318,599, filed as application No. PCT/EP2015/064796 on Jun. 30, 2015, now Pat. No. 11,077,216, application No. 16/997,188, which is a division of application No. 16/288,650, filed on Feb. 28, 2019, now abandoned, which is a division of application No. 14/367,649, filed as application No. PCT/EP2012/076689 on Dec. 21, 2012, now abandoned.

(30) Foreign Application Priority Data

Dec. 21, 2011  (WO) ................. PCT/EP2011/073670
Jun. 30, 2014  (GB) ..................................... 1411569

(51) Int. Cl.
  *A61K 51/00*   (2006.01)
  *A61M 36/14*   (2006.01)
  *A61K 47/12*   (2006.01)
  *A61K 51/04*   (2006.01)

(52) U.S. Cl.
  CPC .......... *A61K 47/12* (2013.01); *A61K 51/0406* (2013.01)

(58) Field of Classification Search
  CPC ............................ A61K 47/12; A61K 51/0406
  USPC ....................................................... 424/1.89
  See application file for complete search history.

(56) References Cited

U.S. PATENT DOCUMENTS

| | | | |
|---|---|---|---|
| 8,182,788 B2 | 5/2012 | Knight et al. | |
| 8,343,459 B2 | 1/2013 | Nakamura et al. | |
| 8,747,809 B2* | 6/2014 | Kung | C07B 59/001 548/530 |
| 8,790,620 B2 | 7/2014 | Hayashi et al. | |
| 10,010,632 B2 | 7/2018 | Ito et al. | |
| 2008/0076914 A1 | 3/2008 | Grigg et al. | |
| 2008/0281121 A1 | 11/2008 | Ito et al. | |
| 2009/0155166 A1 | 6/2009 | McBride et al. | |
| 2009/0198085 A1 | 8/2009 | Hayashi et al. | |
| 2012/0065365 A1 | 3/2012 | Chen et al. | |

FOREIGN PATENT DOCUMENTS

| | | |
|---|---|---|
| AU | 2006262425 B2 | 12/2011 |
| CA | 2651786 A1 | 11/2007 |
| CN | 1646175 A | 7/2005 |
| CN | 101636183 A | 1/2010 |
| EP | 2119458 A1 | 11/2009 |
| JP | 2006500319 A | 1/2006 |
| JP | 2008546783 A | 12/2008 |
| JP | 5159636 B2 | 3/2013 |
| JP | 5258583 B2 | 8/2013 |
| KR | 20090111331 A | 10/2009 |
| RU | 2008148851 A | 6/2010 |
| RU | 2428415 C2 | 9/2011 |
| WO | 2003090789 A1 | 6/2003 |
| WO | 03090789 A1 | 11/2003 |
| WO | 2005009393 A2 | 2/2005 |
| WO | 2006037950 A1 | 4/2006 |
| WO | 2007001958 A3 | 5/2007 |
| WO | 2008075522 A1 | 6/2008 |
| WO | 2008099800 A1 | 8/2008 |
| WO | 2012089594 A1 | 7/2012 |
| WO | 2013053941 A1 | 4/2013 |

(Continued)

OTHER PUBLICATIONS

European Search Report received Application No. 20196030.9-1109 dated Aug. 12, 2020, 6 pages.
Channing et al., Nuc. Med. Biol., [no date] 2001, 28, 469-471.
Chinese Office Action (Second) corresponding to CN Application No. 201280063530.X (PCT/EP2012/076689), dated Dec. 21, 2012. (translation).
Chinese Search Report corresponding to CN Application No. 201280063530.X, dated Dec. 21, 2012. (translation).

(Continued)

*Primary Examiner* — Michael G. Hartley
*Assistant Examiner* — Sean R Donohue
(74) *Attorney, Agent, or Firm* — Culhane Meadows, PLLC; Jeff B. Vockrodt (57) ABSTRACT

The present invention provides a novel method for the preparation of $^{18}$F-fluoride (18F) for use in radiofluorination reactions. The method of the invention finds use especially in the preparation of 18F-labelled positron emission tomography (PET) tracers. The method of the invention is particularly advantageous where bulk solutions are prepared and stored in prefilled vials rather than being freshly prepared on the day of synthesis. Also provided by the present invention is a radiofluorination reaction which comprises the method of the invention, as well as a cassette for use in carrying out the method of the invention and/or the radiofluorination method of the invention on an automated radiosynthesis apparatus.

9 Claims, 2 Drawing Sheets

(56) References Cited

FOREIGN PATENT DOCUMENTS

| WO | 2013093025 A1 | 6/2013 |
|---|---|---|
| WO | 2013144301 A2 | 10/2013 |
| WO | 2014023775 A1 | 2/2014 |

OTHER PUBLICATIONS

Decision to Grant a Patent for an Invention from the Patent Office of the Russian Federation (ROSPATENT), along with the corresponding English translation for Russian Patent Application No. 2014118755/15(029583), filed Dec. 12, 2012.
European Office Action corresponding to EP Application No. 12806500.0, dated Jan. 29, 2018.
European Search Report corresponding to European Application No. 18187551.9, dated Jan. 21, 2019.
GB Search Report regarding GB Application No. 1411569.5, dated Mar. 31, 2015, 5 pages.
Gomzina, et al., Radiochem, [no date] 2002, 44, 403-409.
Great Britain combined Search and Examination Report corresponding to GB Application No. GB1810553.6, dated Jul. 26, 2018.
International Search Report and Written Opinion corresponding to PCT Application No. PCT/EP2012/076689, dated Mar. 8, 2013.
International Search Report and Written Opinion regarding International Application No. PCT/EP2015/064796, dated Sep. 15, 2015, 8 pages.
Japan Decision of Rejection corresponding to Japanese Application No. 2016-573925, dated Apr. 24, 2020 (with English translation).
Klok et al., Appl. Rad. Isot. 66 (2008) 203-207.
Korea Notice of Preliminary Rejection corresponding to KR Application No. 10-2014-7016663, dated Dec. 5, 2018.
Korea Notice of Preliminary Rejection corresponding to KR Application No. 10-2014-7016663, dated Dec. 5, 2018 (translation).
Lasa et al., Tetrahedron: Asymmetry.
Lemaire et al., J. Label. Compd Radiopharm. 2002, 45, 435-447.
McConathy et al. Appl. Rad. Isot. 58 (2003) 657-666.
Meyer et al. Appl. Rad. Isot.1999, 51, 37-41.
Nakao et al., App. Rad. Isot. 62 (2005) 889-895.
Nakao, et al., Appl. Rad. Isot. 62 (2005) 889-895.
Oh et al., Nucl. Med. Biol. 31 (2004) 803-809.
Stocking et al. Tetrahedron 57 (2001) 5303-5320.
Svadberg et al., "Degradation of acetonitrile in eluent solutions for [18F] fluoride PET chemistry: impact on radiosynthesis of [18] FACBC and [18F] FDG," Journal of Labelled Compounds and Radiopharmaceuticals, vol. 55, 2012, pp. 97-102.
Vallabhajosula et al., Mol. Imaging: Radiopharm. PET and SPECT.
Wickstrom, et al., "The development of an automated and optimized synthesis of [18F] Fluciclovine on a FASTlab synthesizer utilizing chemometric design," The Journal of Nuclear Medicine, vol. 40, No. 2, 331-333, 2011.
Intention to Grant Corresponding EP Application No. 18 187 551.9-1109 dated Sep. 7, 2020.
Russian Office Action received in Application No. 2020123031.4 dated Nov. 20, 2020, 12 pages.
Russian Search Report received in Application No. 2020123031.4 dated Jun. 30, 2015, 4 pages.
Svadbert, et al., "Degradation of acetonitrile in eluent solutions for [18F]fluoride PET chemistry: impact on radiosynthesis of [18F]FACBC and [18F]FDG," Research Article, Oct. 20, 2011, 6 pages.

\* cited by examiner

FORMULATION AND METHOD OF SYNTHESIS

This application is a continuation-in-part of U.S. application Ser. No. 15/318,599 filed Dec. 13, 2016, which is a national stage of PCT/EP2015/064796 filed Jun. 30, 2015, which claims priority to UK Patent Application No. 1411569.5 filed Jun. 30, 2014; this application is a continuation-in-part of U.S. application Ser. No. 16/288,650 filed Feb. 28, 2019, which is a divisional of U.S. application Ser. No. 14/367,649 filed Jun. 20, 2014, which is a national stage of PCT/EP2012/076689 filed Dec. 21, 2012, which claims priority to PCT/EP2011/073670 filed Dec. 21, 2011. The disclosures of each of the above applications are incorporated herein in their entirety.

TECHNICAL FIELD OF THE INVENTION

The present invention relates to a drug product composition and in particular to a composition comprising a positron emission tomography (PET) tracer. The composition of the present invention and its method of synthesis have certain advantages over the prior art.

DESCRIPTION OF RELATED ART

The non-natural amino acid $^{18}$F-1-amino-3-fluorocyclobutane-1-carboxylic acid $^{18}$F-FACBC, also known as $^{18}$F-Fluciclovine is taken up specifically by amino acid transporters and shows promise for positron emission tomography (PET) imaging of prostate cancer (Nanni et al 2014 Clinical Genitourinary Cancer; 12(2): 106-110).

Production of $^{18}$F-FACBC comprises labelling of a triflate precursor compound with $^{18}$F-fluoride:

before removal of the two protecting groups:

Following the deprotection steps purification is carried out to remove impurities. In the currently-practiced methods a combination of solid phases is used: ion retardation to remove excess Na$^+$ and excess Cl$^-$ left over from the deprotection steps, alumina to remove $^{18}$F-fluoride and a reversed phase to remove FACBC-related impurities such as 1-amino-3-hydroxyl-cyclobutane-1-carboxylic acid (hydroxyl-ACBC) and 1-amino-3-chloro-cyclo butane-1-carboxylic acid (chloro-ACBC).

Figure 1:
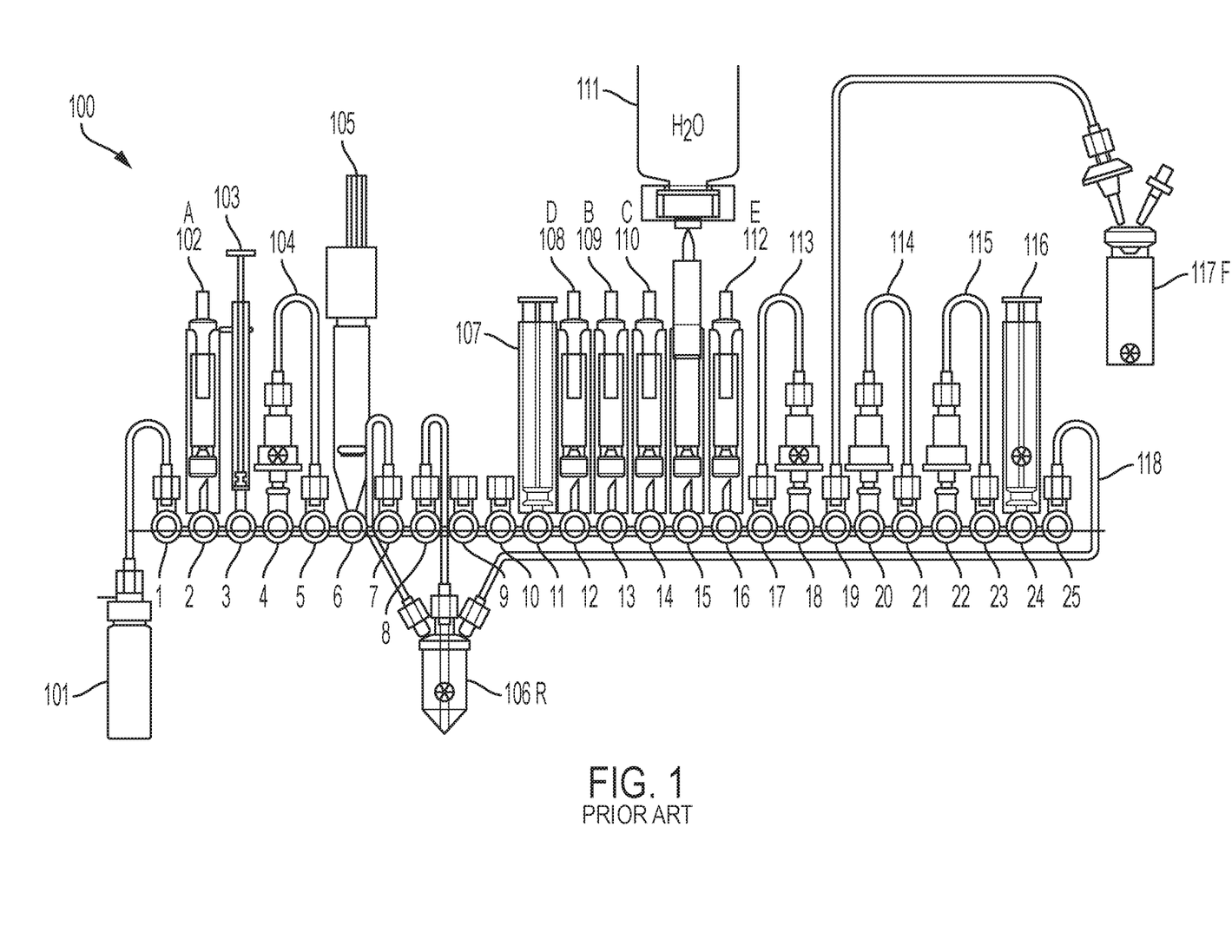
FIG. 1 shows a FASTlab™ cassette of prior art.

The synthesis is currently typically carried out by means of an automated radiosynthesis procedure employing a so-called "cassette" or "cartridge" designed to fit removably and interchangeably onto an automated synthesis apparatus such as those that are commercially available from GE Healthcare, CTI Inc, Ion Beam Applications S.A. (Chemin du Cyclotron 3, B-1348 Louvain-La-Neuve, Belgium); Raytest (Germany) and Bioscan (USA). The cassette comprises all the reagents, reaction vessels and apparatus necessary to carry out the preparation of $^{18}$F-FACBC following introduction of suitably prepared $^{18}$F-fluoride by methods well-known in the field of PET tracer production. A known cassette for the synthesis of $^{18}$F-FACBC is a FASTlab™ cassette from GE Healthcare is shown in FIG. 1.

The present inventors have found that the quality of the final $^{18}$F-FACBC drug product obtained using the above-described known FASTlab™ cassette and process can be somewhat variable. Residual acetonitrile levels have been found to range from about 100 µg/ml to about 600 µg/ml. While acceptable in terms of permitted daily exposure and in the context of the acceptance criteria for $^{18}$F-FACBC drug product, the amount and observed variability is less than ideal.

The present inventors have also found that residual aluminum have been found to range from about 7 µg/ml to nearly 20 µg/ml, which would mean a potential amount of 100 µg in a 5 ml $^{18}$F-FACBC. Where the $^{18}$F-FACBC drug product also comprises citrate buffer, complexes of aluminum and citrate are likely to be present, which is problematic as it is known that such complexes cross the blood-brain barrier (Rengel 2004 Biometals; 17: 669-689).

There is therefore scope to for an improved $^{18}$F-FACBC drug product formulation.

SUMMARY OF THE INVENTION

The present invention provides a drug product composition comprising $^{18}$F-FACBC that overcomes the problems seen with known such compositions. In particular, the composition of the present invention has an improved impurity profile, making it safer and more effective for imaging as compared with the prior art. Low and predictable levels of acetonitrile and/or aluminum in the final drug product mean that the composition of the invention more easily meets worldwide pharmacopeia requirements. In addition to a significant reduction in the concentration of aluminum in the final drug product, removal of the alumina cartridge has the allied advantages that a shorter and simplified process is permitted and that no particles arising from this cartridge are present, which the present inventors have noted can block the sterile filter used prior to injection of the drug product. Furthermore, the advantages of the present invention are achieved with only minor changes to the known process and without impairing the desirable qualities of known $^{18}$F-FACBC compositions.

DETAILED DESCRIPTION OF THE PREFERRED EMBODIMENTS

To more clearly and concisely describe and point out the subject matter of the claimed invention, definitions are provided in the detailed description hereinbelow for specific terms used throughout the present specification and claims. Any exemplification of specific terms herein should be considered as non-limiting examples.

In one aspect the present invention relates to a positron emission tomography (PET) tracer composition comprising anti-1-amino-3-$^{18}$F-fluorocyclo butyl-1-carboxylic acid ($^{18}$F-FACBC) characterized in that said composition comprises no more than 5.0 µg/mL dissolved aluminum (Al).

In another aspect, the present invention relates to a PET tracer composition comprising (18F-FACBC) which comprises 50-100 mM citrate buffer and has a pH of 4.0-5.0. Preferably the composition has 60-90 mM citrate buffer, most preferably 75-85 mM citrate buffer. Preferably the composition has a pH of 4.0 or more, and more preferably 4.3-4.4.

In one aspect the present invention relates to a positron emission tomography (PET) tracer composition comprising anti-1-amino-3-$^{18}$F-fluorocyclobutyl-1-carboxylic acid ($^{18}$F-FACBC) characterized in that said composition comprises no more than 5.0 µg/mL dissolved aluminum (Al) and no more than 50 µg/mL acetonitrile (MeCN).

In the context of the present invention a "PET tracer composition" refers to a composition comprising a PET tracer together with a biocompatible carrier in a form suitable for mammalian administration. The PET tracer composition of the invention is referred to hereunder also as the composition of the invention. A "PET tracer" is defined herein as a biologically active molecule comprising an atom which is a positron emitter suitable for intravenous administration to a mammalian subject followed by PET imaging to obtain one or more clinically-useful images of the location and/or distribution of the PET tracer. A "biocompatible carrier" as defined herein is a fluid, especially a liquid, in which a pharmaceutical is suspended or dissolved, such that the composition is physiologically tolerable, i.e. can be administered to the mammalian body without toxicity or undue discomfort. The biocompatible carrier is suitably an injectable carrier liquid such as sterile, pyrogen-free water for injection or an aqueous solution such as saline.

The compound "$^{18}$F-FACBC" is represented by the following chemical structure:

The term "not more than" as used herein should be understood to mean any amount less than and including the quoted quantity. In an idealized embodiment of the composition of the present invention. there would be zero µg/mL of each impurity present. However, in reality, zero µg/mL of an impurity is unlikely and at least a trace amount of each impurity remains in the composition. The term "not more than" acknowledges that a trace amount of one or more impurities is present in a PET tracer composition, and defines a concentration limit above which the composition would not be deemed acceptable for use.

In one embodiment, the composition of the invention comprises not more than not more than 3.0 µg/mL dissolved Al, and in another embodiment not more than 1.5 µg/mL dissolved Al.

In one embodiment the composition of the present invention comprises MeCN at a concentration not more than 20 µg/mL.

The composition of the invention in one embodiment has an end of synthesis (EOS) radiochemical purity (RCP) of at least 95%, in another embodiment at least 98%, and in yet another embodiment at least 99%. The composition preferably also has a radioactive concentration (RAC) of at least 1000 MBq/mL, alternatively at least 1500 MBq/ml.

The term "end of synthesis" refers to the point in time when the labelled compound is collected in the product collection vial.

The pharmaceutical composition of the present invention has a favorable impurity profile, with the main non-radioactive impurities being 1-amino-3-hydroxyl-cyclobutane-1-carboxylic acid (hydroxyl-ACBC), 1-amino-3-fluoro-cyclobutane-1-carboxylic acid (FACBC) and 1-amino-3-chloro-cyclobutane-1-carboxylic acid (chloro-ACBC).

It is preferred that there is not more than 150 µg/mL hydroxyl-ACBC, most preferably not more than 80 µg/mL hydroxyl-ACBC.

It is preferred that there is not more than 0.15 µg/mL FACBC, most preferably not more than 0.10 µg/mL FACBC.

It is preferred that there is not more than 2.0 µg/mL chloro-ACBC, most preferably not more than 1.0 µg/mL chloro-ACBC.

The term "aluminum breakthrough" refers to aluminum ions present in the product resulting from partial breakdown of the alumina column. The term refers to a concentration of aluminum in the end-product higher than that found when an alumina column is not used.

The term "not more than" should be understood to mean any amount less than the quoted quantity. Therefore, not more than 100 µg/mL means any amount between 0-100 µg/mL, and in an ideal embodiment of the composition of the present invention there would be zero µg/mL of each impurity present in the composition of the invention. However, in reality, zero µg/mL of an impurity might not be achievable and it is more likely that at least a trace amount of the impurity remains in the composition, i.e. in the case of hydroxyl-ACBC the term not more than 150 µg/mL covers e.g. 50-150 µg/mL, not more than 0.10 µg/mL for FACBC covers e.g. 0.05-0.10 µg/mL, and not more than 1.0 µg/mL chloro-ACBC covers e.g. 0.25-1.0 µg/mL.

An advantage of the composition of the present invention is that the pH, stability and impurity profile can be kept within a very narrow range over a long shelf-life, at high activities, and when manipulated e.g. by autoclaving or by dilution with 0.9% saline.

In a preferred embodiment, the pharmaceutical composition of the invention does not comprise a radiostabilizer. It is common for pharmaceutical compositions comprising radioactive pharmaceuticals to include a radiostabilizer. For example, known pharmaceutical compositions of [$^{18}$F] FACBC include a sugar alcohol or a sugar lactone.

EP 2080526 (A1) discloses that radiolysis can be inhibited by adding a sugar lactone such as ascorbic acid and glucono-o-lactone to [$^{18}$F]FACBC, and BP 2119458 (A1) discloses that a sugar alcohol such as erythritol xylitol, sorbitol or mannitol can be added as an additive to inhibit radiolysis and improve stability. No such radiostabilizer is required in the radiopharmaceutical composition of the present invention in order to maintain a shelf-life of up to around 10 hours.

EP 2119458 (A1) teaches that a more stable formulation of $^{18}$F-FACBC is achieved when the pH is maintained within the range 2.0-5.9. As discussed in WO 2013/093025, use of citrate buffer allows the pH to be maintained within an even narrower range, provides resistance to degradation and enables the formulation to be autoclaved. In one embodiment, the composition of the present invention therefore comprises around 50-100 mM citrate buffer, in another embodiment around 60-90 mM citrate buffer and in yet another embodiment around 75-85 mM citrate buffer. The term "around" in this context incorporates the exact values of the ranges as well as a small variation around these values that would be expected by the skilled person to achieve the same stabilization effect.

In another aspect, the present invention provides a method to prepare a PET tracer composition of the invention wherein said method comprises:

a) reacting in a reaction vessel a source of $^{18}$F-fluoride with a precursor compound of Formula I:

(I)

wherein:
LG is a leaving group;
PG1 is a carboxy protecting group; and,
PG2 is an amine protecting group;
to obtain a reaction mixture comprising a compound of Formula II:

(II)

wherein PG1 and PG2 are as defined for Formula I;

b) carrying out removal of PG1 and PG2 to obtain a reaction mixture comprising $^{18}$F-FACBC; and c) purifying said reaction mixture comprising $^{18}$F-FACBC by passing it through a hydrophilic lipophilic balanced (HLB) solid phase, characterized in that said purifying does not comprise passing the reaction mixture comprising $^{18}$F-FACBC through an alumina solid phase.

In another aspect, the present invention provides a method to prepare a PET tracer composition of the invention wherein said method comprises:

a) reacting in a reaction vessel a source of $^{18}$F-fluoride with a precursor compound of Formula I:

(I)

wherein
LG is a leaving group;
PG1 is a carboxy protecting group; and, PG2 is an amine protecting group;
wherein said reacting step is carried out in acetonitrile;
to obtain a reaction mixture comprising a compound of Formula II:

(II)

wherein PG1 and PG2 are as defined for Formula I;

b) transferring said reaction mixture comprising said compound of Formula II out of said reaction vessel and carrying out removal of PG1 to obtain a reaction mixture comprising a compound of Formula III:

(III)

wherein PG2 is as defined for Formula I;

c) applying heat to said reaction vessel at the same time as carrying out removal of PG1;

d) transferring said reaction mixture comprising said compound of Formula III back into said reaction vessel and carrying out removal of PG2 to obtain a reaction mixture comprising $^{18}$F-FACBC;

e) purifying said reaction mixture comprising $^{18}$F-FACBC by passing it through a hydrophilic lipophilic balanced (HLB) solid phase, characterized in that said purifying does not comprise passing the reaction mixture comprising $^{18}$F-FACBC through an alumina solid phase.

The "source of $^{18}$F-fluoride" suitable for use in step (a) of the method of the invention is normally obtained as an aqueous solution from the nuclear reaction $^{18}$O(p,n)$^{18}$F. In order to increase the reactivity of fluoride and to reduce or minimize hydroxylated by-products resulting from the presence of water, water is typically removed from 18F-fluoride prior to the reaction, and fluorination reactions are carried out using anhydrous reaction solvents (Aigbirhio et al 1995 J Fluor Chem; 70: 279-87). A further step that is used to improve the reactivity of $^{18}$F-fluoride for radiofluorination reactions is to add a cationic counterion prior to the removal of water. Suitably, the counterion should possess sufficient solubility within the anhydrous reaction solvent to maintain the solubility of the $^{18}$F-fluoride. Therefore, counterions that are typically used include large but soft metal ions such as rubidium or cesium, potassium complexed with a cryptand such as Kryptofix™, or tetraalkylammonium salts, wherein potassium complexed with a cryptand such as Kryptofix™, or tetraalkylammonium salts are preferred.

The "precursor compound" for step (a) of the method of the invention comprises a non-radioactive derivative of a radiolabeled compound, designed so that chemical reaction with a convenient chemical form of the detectable label occurs site-specifically, can be conducted in the minimum number of steps (ideally a single step), and without the need for significant purification (ideally no further purification), to give the desired radiolabeled compound. Such precursor compounds are synthetic and can conveniently be obtained in good chemical purity.

A suitable "leaving group" in the context of the compound of Formula I in step (a) of the method of the present invention is a chemical group that can be displaced by nucleophilic displacement reaction with fluoride ion. These are well-known in the art of synthetic chemistry. In some embodiments the leaving group of the present invention is a linear or branched $C_{1-10}$ haloalkyl sulfonic acid substituent, a linear or branched $C_{1-10}$ alkyl sulfonic acid substituent, a fluorosulfonic acid substituent, or an aromatic sulfonic acid substituent. In other embodiments of the invention the leaving group is selected from methanesulfonic acid, toluenesulfonic acid, nitrobenzenesulfonic acid, benzenesulfonic acid, trifluoromethanesulfonic acid, fluorosulfonic acid, and perfluoroalkylsulfonic acid. In some embodiments the leaving group is either methanesulfonic acid, trifluoromethanesulfonic acid or toluenesulfonic acid and in another embodiment the leaving group is trifluoromethanesulfonic acid.

The term "protecting group" as used in connection with the substituents PG1 and PG2 refers to a group which inhibits or suppresses undesirable chemical reactions, but which is designed to be sufficiently reactive that it may be cleaved from the functional group in question to obtain the desired product under mild enough conditions that do not modify the rest of the molecule. Protecting groups are well known to those skilled in the art and are described in 'Protective Groups in Organic Synthesis', Theorodora W. Greene and Peter G. M. Wuts, (Fourth Edition, John Wiley & Sons, 2007).

The PG1 "carboxy protecting group" herein is preferably linear or branched C 1-10 alkyl chain or an aryl substituent. The term "alkyl" used either alone or as part of another group is defined as any straight, branched or cyclic, saturated or unsaturated CnHzn+1 group. The term "aryl" refers to any C6-14 molecular fragment or group which is derived from a monocyclic or polycyclic aromatic hydrocarbon, or a monocyclic or polycyclic heteroaromatic hydrocarbon. In one embodiment of the method of the invention PG1 is selected from methyl, ethyl, t-butyl and phenyl. In another embodiment of the invention PG1 is methyl or ethyl and in yet another embodiment PG1 is ethyl.

The PG2 "amine protecting group" herein refers to a chemical group that suitably prevents reaction between 18F and the amino group in the process of providing the compound of Formula II. Examples of suitable amine protecting groups include various carbamate substituents, various amide substituents, various imide substituents, and various amine substituents. Preferably, the amine protecting group is selected from the group consisting of linear or branched $C_{2-7}$ alkyloxycarbonyl substituents, linear or branched $C_{3-7}$ alkenyloxycarbonyl substituents, $C_{7-12}$ benzyloxycarbonyl substituents that may have a modifying group, $C_{2-7}$ alkyldithiooxycarbonyl substituents, linear or branched $C_{1-6}$ alkylamide substituents, linear or branched $C_{2-6}$ alkenylamide substituents, $C_{6-11}$ benzamide substituents that may have a modifying group, $C_{4-10}$ cyclic imide substituents, $C_{6-11}$ aromatic imine substituents that may have a substituent, linear or branched $C_{1-6}$ alkylamine substituents, linear or branched $C_{2-6}$ alkenylamine substituents, and $C_{6-11}$ benzylamine substituents that may have a modifying group. In some embodiments of the invention $PG^2$ is selected from t-butoxycarbonyl, allyloxycarbonyl, phthalimide, and N-benzylideneamine. In other embodiments $PG^2$ is selected from t-butoxycarbonyl or phthalimide. In one embodiment of the invention $PG^2$ is t-butoxycarbonyl.

The term "reacting" in step (a) of the method of the invention as is well known to those of skill in the art refers to bringing two or more chemical substances (typically referred to in the art as "reactants" or "reagents") together to result in a chemical change in one or both/all of the chemical substances.

The "removal of PG1 in step (b) of the method of the invention is suitably carried out by contacting the compound of Formula II, comprised within the reaction mixture obtained in step (a), with a carboxy deprotecting agent. A suitable carboxy deprotecting agent may be either an acid or an alkaline solution, as is well-known to the skilled person (see Greene and Wuts, supra). The concentration of the carboxy deprotecting agent is suitably just sufficient to remove the carboxy protecting group. Preferably the carboxy deprotecting agent is an alkaline solution. In certain embodiments the carboxy deprotecting agent is a sodium hydroxide or a potassium hydroxide solution and in a preferred embodiment is a sodium hydroxide solution, for example of 0.5-2.0M. The temperature and the duration used for deprotection may in some embodiments be tailored to permit removal of PG1. For example, in certain embodiments the reacting step is carried out at room temperature and for a duration of around 1-5 minutes. In one embodiment, removal of PG1 is carried out by passing the reaction mixture comprising the compound of Formula II through a solid phase extraction (SPE) column where the compound of Formula II binds to the solid phase. Once the compound of Formula II is bound, the outlet of the SPE column is closed so that the carboxy deprotecting agent is retained therein for a defined amount of time. A suitable solid phase for use in this manner is a reversed phase solid phase, e.g. tC18.

Step (c) comprises applying heat to the reaction vessel using methods well-known to those of skill in the art, e.g. using a dedicated heater into which the reaction vessel is placed for the duration of the radiosynthesis. The application of heat must be so that the reaction vessel can be used for the subsequent step (d), i.e. so that the reaction vessel is intact and undamaged, and also so that residual solvent is effectively removed. This step (c) is carried out at the same time as removal of PG1, i.e. after the reaction mixture comprising the compound of Formula II has been transferred out of said reaction vessel. A suitable temperature for this heating step should be no greater than the tolerance of the reaction vessel, e.g. for a reaction vessel made from cyclic olefin copolymer (COC) a temperature of no greater than about 130° C. and for a reaction vessel made from polyetheretherketone (PEEK) a temperature of no greater than about 200° C. For convenience, the temperature used to heat the reaction vessel in step (c) may be selected to be as close as possible to the temperature used during the labelling step (a). Suitable temperatures for radiolabeling step (a) are in the range of about 80-140° C., in other embodiments 85-130° C.

The "removal of PG2 in step (d) of the method of the invention is carried out by contacting the compound of Formula III with an amine deprotecting agent. A suitable amine deprotecting agent may be either an acid or an alkaline solution, as is well-known to the skilled person (see Greene and Wuts, supra). The concentration of the amine deprotecting agent is suitably just sufficient to remove PG2. Preferably the amine deprotecting agent is an acid solution. A suitable acid is an acid selected from inorganic acids such as hydrochloric acid (HCl), sulfuric acid (H2SO4) and nitric acid (HNO3), and organic acids such as perfluoroalkyl carboxylic acids, e.g. trifluoroacetic acid (CF3CO2H). In certain embodiments, the amine deprotecting agent is HCl, e.g. at a concentration of 1.0-4.0M. Removal of PG2 is in one embodiment carried out with heat to allow the deprotection to proceed more rapidly. The time depends on the reaction temperature or other conditions. For example, in one embodiment removal of PG2 is carried out at 60° C., with a reaction time of 5 minutes.

The aim of the "purifying" step (e) is to obtain substantially pure $^{18}$F-FACBC. The term "substantially" refers to the complete or nearly complete extent or degree of an action, characteristic, property, state, structure, item, or result. The term "substantially pure" as used herein in the context of $^{18}$F-FACBC encompasses completely pure 18F-FACBC or $^{18}$F-FACBC that is sufficiently pure to be suitable for use as a PET tracer. The term "suitable for use as a PET tracer" means that the purified $^{18}$F-FACBC product is suitable for intravenous administration to a mammalian subject followed by PET imaging to obtain one or more clinically-useful images of the location and/or distribution of $^{18}$F-FACBC.

A suitable purifying step comprises:
  i. carrying out a first purification step comprising passing said reaction mixture through a hydrophilic lipophilic balanced (HLB) solid phase; and,
  ii. optionally carrying out a second purification step comprising passing said reaction mixture through an alumina solid phase.

A "HLB solid phase" is a reversed phase solid phase having hydrophilic and lipophilic components suitable for a range of purposes. HLB solid phase is commercially available as SPE cartridges suitable for use in the method of the present invention, e.g. the Oasis HLB SPE cartridge.

An "alumina solid phase" is an aluminum oxide normal phase solid phase routinely used in 18F labelling methods as a means to remove free $^{18}$F-fluoride and optimize the radiochemical purity of the final product. Alumina solid phase is commercially-available as SPE cartridges suitable for use in the method of the present invention, e.g. the Waters Alumina N Light.

In the method of the invention, steps (a)-(c) or (a)-(e) are carried out in sequence.

In one embodiment of the method of the present invention, the substituent LG in the compound of Formula I is a linear or branched $C_{1-10}$ haloalkyl sulfonic acid substituent, a linear or branched $C_{1-10}$ alkyl sulfonic acid substituent, a fluorosulfonic acid substituent, or an aromatic sulfonic acid substituent. Examples of LG include methanesulfonic acid, toluenesulfonic acid, nitrobenzenesulfonic acid, benzenesulfonic acid, trifluoromethanesulfonic acid, fluorosulfonic acid, and perfluoroalkylsulfonic acid. In one embodiment LG is trifluoromethanesulfonic acid.

In one embodiment of the method of the present invention the substituent PG1 in the compounds of Formula I and II is a linear or branched $C_{1-10}$ alkyl chain or an aryl substituent. For example, PG1 can be methyl, ethyl, t-butyl or phenyl. In one embodiment PG1 is methyl or ethyl. In another embodiment, PG1 is ethyl.

In one embodiment of the method of the present invention the substituent PG2 in the compounds of Formulas I-III is a carbamate substituent, an amide substituent, an imide substituent or an amine substituent. Examples include t-butoxycarbonyl, allyloxycarbonyl, phthalimide, and N-benzylideneamine. In one embodiment, PG2 is t-butoxycarbonyl.

The method of the present invention may further comprise the step of formulating the purified reaction mixture obtained in step (e) with citrate buffer. In one embodiment, this formulating step results in a concentration of 50-100 mM citrate buffer, in another embodiment 60-90 mM citrate buffer and in yet another embodiment 75-85 mM citrate buffer.

In one embodiment, the method of the invention is automated, e.g. carried out on an automated synthesis apparatus. $^{18}$F-labelled PET tracers are often conveniently prepared on automated radiosynthesis apparatus. By the term "automated radiosynthesis apparatus" is meant an automated module based on the principle of unit operations as described by Satyamurthy et al (1999 Clin Positr Imag; 2(5): 233-253). A known method for production of $^{18}$F-FACBC drug product using this FASTlab™ cassette is described in Example 1 of WO 2013/093025.

The term "unit operations" means that complex processes are reduced to a series of simple operations or reactions, which can be applied to a range of materials. Suitable automated synthesiser apparatus are commercially available from a range of suppliers including: GE Healthcare Ltd (Chalfont St Giles, UK); CTI Inc. (Knoxville, USA); Ion Beam Applications S.A. (Chemin du Cyclotron 3, B-1348 Louvain-La-Neuve, Belgium); Raytest (Straubenhardt, Germany) and Bioscan (Washington D.C., USA).

Commercial automated radiosynthesis apparatus also provide suitable containers for the liquid radioactive waste generated as a result of the radiopharmaceutical preparation. Automated radiosynthesis apparatus are not typically provided with radiation shielding, since they are designed to be employed in a suitably configured radioactive work cell. The radioactive work cell, also termed a hot cell, provides suitable radiation shielding to protect the operator from potential radiation dose, as well as ventilation to remove chemical and/or radioactive vapours.

The automated synthesis apparatus preferably comprises a cassette. By the term "cassette" is meant a piece of apparatus designed to fit removably and interchangeably onto an automated synthesis apparatus, in such a way that mechanical movement of moving parts of the synthesizer controls the operation of the cassette from outside the cassette, i.e. externally. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesis apparatus. External rotation of the arm thus controls the opening or closing of the valve when the cassette is attached to the automated synthesis apparatus. Additional moving parts of the automated. synthesis apparatus are designed to clip onto syringe plunger tips, and thus raise or depress syringe barrels.

The cassette is versatile, typically having several positions where reagents can be attached, and several suitable for attachment of syringe vials of reagents or chromatography cartridges (e.g. for SPE). The cassette always comprises a reaction vessel. Such reaction vessels are preferably 0.5 to 10 mL, more preferably 0.5 to 5 mL and most preferably 0.5 to 4 mL in volume and are configured such that 3 or more ports of the cassette are connected thereto, to permit transfer of reagents or solvents from various ports on the cassette. Preferably the cassette has 15 to 40 valves in a linear array, most preferably 20 to 30, with 25 being especially preferred. The valves of the cassette are preferably each identical, and most preferably are 3-way valves. The cassettes are designed to be suitable for radiopharmaceutical manufacture and are therefore manufactured from materials which are of pharmaceutical grade and ideally also are resistant to radiolysis.

Preferred automated radiosynthesis apparatus of the present invention are those which interact with a disposable or single use "cassette" (also commonly referred to as a "cartridge") which comprises all the reagents, reaction vessels and apparatus necessary to carry out the preparation of a given batch of radiopharmaceutical. By use of such cassettes the automated radiosynthesis apparatus has the flexibility to be capable of making a variety of different radiopharmaceuticals with minimal risk of cross-contamination, by simply changing the cassette. The cassette approach also has the advantages of: simplified set-up and hence reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, tamper and abuse resistance.

The cassette has been simplified by removal of the alumina cartridge. The alumina cartridge was present in prior cassette configurations to remove residues of free 18F-fluoride from insufficient purification and/or from radiolysis. However, the present inventors have found that the rest activity on the alumina cartridge is very low (0.1-0.3%) indicating both a robust purification process and a low degree of radiolysis. These data suggest that the alumina cartridge is superfluous and can be removed. This has the additional benefit of there being no risk of any particles from the alumina cartridge being present in drug product, which pose a risk of blocking the sterile filter.

The process has been improved by the addition of a concurrent step of removal of residual acetonitrile from the reactor while the deesterification step proceeds on the tC18 cartridge. This results in a final drug product having a lower and more predictable concentration of residual acetonitrile than that obtained using prior art methods.

BRIEF DESCRIPTION OF THE EXAMPLES

The following non-limiting examples serve to illustrate particular embodiments of the subject matter of the present invention.

List of Abbreviations Used in the Examples

ATR attenuated total reflectance
DTGS deuterated triglycine sulphate
[$^{18}$F]FACBC 1-amino-3-[$^{18}$F]fluorocyclobutane-I-carboxylic acid
FT-IR Fourier transform infrared
K.222
BOC tert-Butyloxycarbonyl
DP drug product
HLB hydrophobic-lipophilic balance
K222 Kryptofix 222
MeCN acetonitrile
MeOH methanol
QMA quaternary methyl ammonium
RCY radiochemical yield
RAC radioactive concentration
RCP: radiochemical purity
SPE solid-phase extraction
TLC thin layer chromatography
UV ultraviolet

EXAMPLES

All reagents and solvents were purchased from Merck and used without further purification. The [$^{18}$F]FACBC precursor, Syn-1-(N-(tert-butoxycarbonyl)amino)-3-[[(trifluoromethyl)sulfonyl]oxy]-cyclobutane-1-carboxylic acid ethyl ester was obtained from GE Healthcare. The Oasis HLB plus cartridge and the Sep-Pak cartridges: QMA light Plus (K.2C03 form), tC18 light, Alumina N light were purchased from Waters (Milford, Mass., USA). A Capintec NaI ion chamber was used for all radioactive measurements (model CRC15R). Radio-thin layer chromatography (radio-TLC) was performed on a Packard instant imager using pre-coated plates of silica gel (Merck 60F254).

Comparative Example 1: Prior Art Synthesis of $^{18}$F-FACBC

1(i) FASTlab Cassette

All radiochemistry was performed on a commercially-available GE FASTlab™ with single-use cassettes, as shown in FIG. 1.

The cassette (100) is built around a one-piece-molded manifold with 25 three-way stopcocks (1-25), all made of polypropylene. Briefly, the cassette includes a 5 ml reactor (106), which is made from cyclic olefin copolymer, one 1 ml syringe (103) and two 5 ml syringes (107, 116), 14 cm tubing to the target recovery vessel (101), a fluoride inlet (105), spikes for connection with five prefilled vials 102 (Vial A), 108 (Vial D), 109 (Vial B), 110 (Vial C), 112 (Vial E), one 100 ml water bag (111) as well as various SPE cartridges: tC18 cartridge (113), alumina cartridge (114), and hydrophilic lipophilic balanced (HLB) cartridge (115) and filters. 42 cm tubing (118) connects to the right-hand side of the reactor vessel. Fluid paths are controlled with nitrogen purging, vacuum and the three syringes. The fully automated system is designed for single-step fluorinations with cyclotron-produced $^{18}$F-fluoride. The FASTlab was programmed by the software package in a step-by-step time-dependent sequence of events such as moving the syringes, nitrogen purging, vacuum, and temperature regulation. Vial A (102) contained K222 (58.8 mg, 156 µmol), K$_2$CO$_3$ (8.1 mg, 60.8 µmol) in 79.5% (v/v) MeCN(aq) (1105 µl). Vial B (109) contained MeCN (4.1 ml). Vial C (110) contained the precursor (48.4 mg, 123.5 µmol) in its dry form (stored at −20° C. until cassette assembly). Vial D (108) contained 4M HCl (2.0 ml). Vial E (112) contained 2 M NaOH (4.1 ml). The 30 ml product collection glass vial (117) was filled with 200 mM trisodium citrate buffer (10 ml).

1(ii) Production of $^{18}$F-Fluoride

No-carrier-added $^{18}$F-fluoride was produced via the 18O (p,n)18F nuclear reaction on a GE PETtrace 6 cyclotron (Norwegian Cyclotron Centre, Oslo). Irradiations were performed using a dual-beam, 30 µA current on two equal Ag targets with HAVAR foils using 16.5 MeV protons. Each target contained 1.6 ml of 2: 96% [$^{18}$O]water (Marshall Isotopes). Subsequent to irradiation and delivery to a hotcell, each target was washed with [$^{16}$O]water (Merck, water for GR analysis). Aqueous $^{18}$F-fluoride (1-1.5 ml, 100-200 Mbq) was passed through the QMA cartridge (104) and into the $^{18}$O—H2O recovery vial (101). The QMA cartridge (104) was then flushed with MeCN and sent to waste.

1(iii)$^{18}$F-Fluoride Labelling

The trapped $^{18}$F-fluoride was eluted into the reactor (106) using 730 µl eluent from vial A (102) and then concentrated to dryness by azeotropic distillation with 80 µl acetonitrile from vial C (110). Approximately 1.7 ml of MeCN was mixed with precursor in vial C (110) from which 1.0 ml of the dissolved precursor (corresponds to 72.7 mmol precursor) was added to the reactor and heated for 3 min to 85° C.

1(iv) Removal of Ester Protecting Group

The reaction mixture was diluted with water and sent through the tC18 cartridge (113). The reactor (106) was washed with water and sent through the tC18 cartridge (113). The labelled intermediate, fixed on the tC18 cartridge (113) was washed with water, and then incubated with 2M NaOH (2.0 ml) for 5 minutes after which the 2M NaOH was sent to waste.

1(v) Removal of BOC Protecting Group

The labelled intermediate (without the ester group) was then eluted off the tC18 cartridge (113) into the reactor (106) using water. The BOC group was hydrolyzed by adding 4M HCl (1.4 ml) and heating the reactor for 5 min at 60° C.

1(vi) Purification

The reactor (106) content with the crude $^{18}$F-FACBC was sent through the HLB (115) and alumina cartridge (114) and into the 30 ml product vial. The HLB cartridge (115) and alumina cartridges (114) were washed with water (9.1 ml total) and collected in the product vial (117).

1(vii) Formulation

2M NaOH and water was added to the product vial (117), giving a purified drug product (DP) with a total volume of 26 ml.

1(viii) Acetonitrile Concentration

Acetonitrile (MeCN) concentration was determined using a gas chromatographic system with FID, an automated liquid injector, a fused silica capillary column with USP stationary phase G43 (6% cyanopropylphenyl-94% dimethyl polysiloxane) and a reporting integrator or data system with reintegration capacity. 1000 µg/ml of MeCN was used as a standard. Blank was prepared by transferring 1 ml of purified water to a 2 ml GC crimp cap vial, which was capped immediately. 1 ml of the standard was transferred to a 2 ml GC crimp cap vials and capped immediately. 0.20 ml of the sample was transferred to a 2 ml GC crimp cap vial with low volume insert (0.25 ml) and capped immediately. The experimental conditions of the GC instrument were as follows:

Carrier gas flow, Helium: 2.0 ml/min

Oven temperature program: 40° C. for 6 minutes then 20° C./min to 240° C. for 4 minutes Injector temperature: 225° C.

Split ratio: 10:1 Detector: FID

Detector temperature: 250° C.

Hydrogen flow rate: 30 ml/min

Air flow rate: 400 ml/min

Make up gas flow rate (He): 25 ml/min

The experimental conditions of the automatic liquid injector were as follows:

Solvent pre-washes: 3

Sample pumps: 3

Solvent post washes: 3 Injection volume: 1 ml

The column was conditioned at 250° C. for at least one hour prior to use.

One injection of each standard and two replicate injections of the sample solution were performed in addition to blank injections in the following order:

Blank

Calibration standard

Calibration standard

Blank

Sample, replicate 1

Sample, replicate 2

Blank

The concentration of each analyte, Csample, was calculated in µg/ml using the following formula:

$$C_{sample} = \frac{A_{sample} \times C_{std}}{A_{std}}$$

where:

Asample: Peak area of the analyte in sample

Cstd: Concentration of the analyte in calibration standard (µg/ml)

Astd: Peak area of the analyte in calibration standard, average of 2 injections

1(ix) Aluminum Concentration

Aluminum concentration was determined by inductively coupled plasma atomic emission spectroscopy (ICP-AES).

1(x) Radiochemical Parameters

Radiochemical purity (RCP) and radioactive concentration (RAC) of $^{18}$F-FACBC were measured.

RCP was determined by thin layer chromatography (TLC). The TLC strip was eluted using a mobile phase consisting of acetonitrile:methanol:water:acetic acid, 20:5:5:1 v/v. The RCP and any radiochemical impurities including $^{18}$F-fluoride were reported as percentages of the net sum of all peaks.

1(xi) Results

The following results were obtained:

| Production # | RAC (MBq/ml) | RCP(¾)TO | MeCN (µg/ml) | Al (µg/ml) |
|---|---|---|---|---|
| 1 | 1915 | t > 99 | 506 | 14 |
| 2 | 1804 | r > 99 | 324 | 14 |
| 3 | 1950 | t > 99 | 302 | 13 |
| 4 | 1698 | t > 99 | 89 | 15 |
| 5 | 1570 | r > 99 | 596 | 17 |
| 6 | 1815 | t > 99 | 218 | 15 |

Example 2 Synthesis of $^{18}$F-FACBC Using Inventive Method

Figure 2:
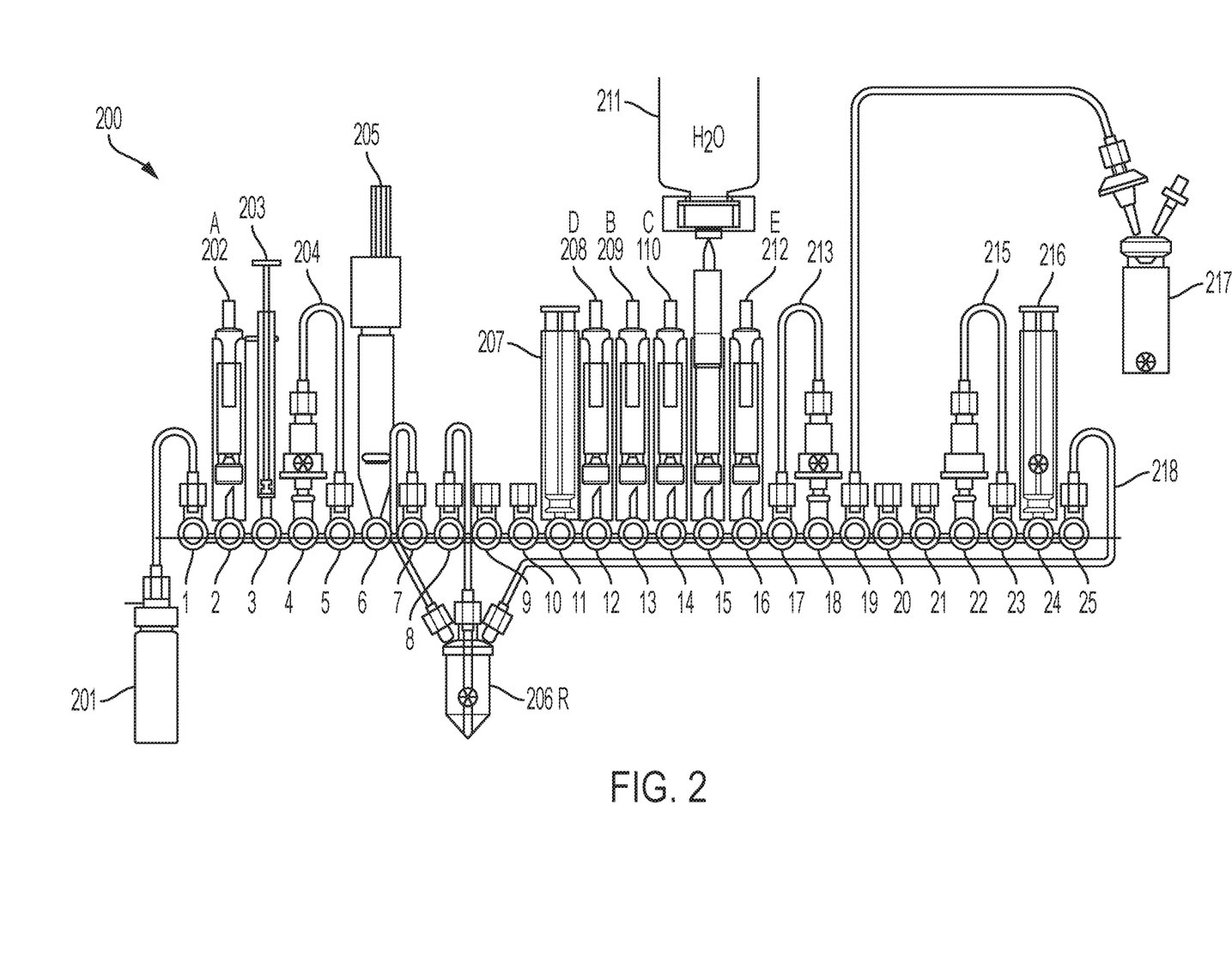
FIG. 2 shows a cassette for producing a radiotracer according to an embodiment of the invention.

A modified FASTlab™ cassette was used, as illustrated in FIG. 2. The cassette (200) is modified relative to that used in Example 1 by removing the alumina column (114) and capping the connectors in its place at positions 20 and 21. The cassette (200) is built around a one-piece-molded manifold with 25 three-way stopcocks (1-25). The cassette (200) includes a reactor (206), one 1 ml syringe (203), and two 5 ml syringes (207, 216), 14 cm tubing to the target recovery vessel (201), a fluoride inlet (205), spikes for connection with five prefilled vials 202 (Vial A), 208 (Vial D), 209 (Vial B), 120 (Vial C), 212 (Vial E), one 200 ml water bag (211) as well as various SPE cartridges: tC18 cartridge (213) and hydrophilic lipophilic balanced (HLB) cartridge (215) and filters. Vial A (202) contained K222 (58.8 mg, 156 µmol), $K_2CO_3$ (8.1 mg, 60.8 µmol) in 79.5% (v/v) MeCN(aq) (1105 µl). Vial B (209) contained MeCN (4.1 ml). Vial C (210) contained the precursor (48.4 mg, 123.5 µmol) in its dry form (stored at −20° C. until cassette assembly). Vial D (208) contained 4M HCl (2.0 ml). Vial E (212) contained 2 M NaOH (4.1 ml). The 30 ml product collection glass vial (217) was filled with 200 mM trisodium citrate buffer (10 ml).

As can be appreciated from FIG. 2, the cassette includes three SPE cartridges: QMA (204), tC18 (213), and HLB (215). Compared to the cassette of FIG. 1, the alumina cartridge has been omitted. Moreover, no other type of SPE is provided in its place. Thus, the crude product is passed to the product vial through only the HLB cartridge (215). The alumina cartridge in the cassette of FIG. 1 is used to remove residual unreactive radioactive fluoride ions, which if present in the end product contribute to low radiochemical purity.

Vial A (202) contained K222 (58.8 mg, 156 µmol), $K_2CO_3$ (8.1 mg, 60.8 µmol) in 79.5% (v/v) MeCN(aq) (1105 µl). Vial B (209) contained 4M HCl (2.0 ml). Vial C (210) contained MeCN (4.1 ml). Vial D (208) contained the precursor (48.4 mg, 123.5 µmol) in its dry form (stored at −20° C. until cassette assembly). Vial E (212) contained 2 M NaOH (4.1 ml). The 30 ml product collection glass vial (217) was filled with 200 mM trisodium citrate buffer (10 ml).

2(i) Modified Sequence

The sequence described in Example 1 was used except that the sequence included the extra heating/purging of the reaction vessel. The hydrolysis step was replaced with two steps, the first step of which included hydrolysis and in parallel heating of the reactor at 85° C., nitrogen purging (600 mbar HF) of the reaction vessel and vacuum (−600 mbar). The second step also included hydrolysis, but heating of the reaction vessel was stopped. Nitrogen purging (600 mbar HF) and vacuum (−600 mbar) were used for cooling of the reaction vessel. Furthermore, the alumina SPE was removed and the sequence was changed to transfer the product directly to the formulation buffer vial after the HLB cartridge step.

2(ii) Analysis

The analysis methods as described in Example 1 were used for Example 2. Notably, the radiochemical purity in Example 2 is similar to that found in Example 1. This is unexpected because the alumina column was thought necessary to trap residual radioactive fluoride ions, which contribute to lower radiochemical purity. This resulting product did not exhibit aluminum breakthrough since the process omitted an alumina column. In other words, the product contained only trace aluminum from the reactants used to manufacture the radiotracer. In addition, it omitted any other column such as an ion retardation column that could be used to remove residual fluoride components.

| Production # | RAC (MBQ/ml) | RCP(¾)TO | MeCN (µg/ml) | Al (µg/ml) |
|---|---|---|---|---|
| 7 | 3112 | 99.1 | 20 | 0.7 |
| 8 | 3900 | 99.1 | 20 | 0.8 |
| 9 | 1631 | 99.1 | 21 | 1.3 |
| 10 | 731 | 99.9 | 22 | 0.8 |
| 11 | 1831 | 99.8 | 25 | 0.8 |
| 12 | 1654 | 99.9 | 24 | 1.3 |
| 13 | 1573 | 99.1 | 21 | 1.1 |
| 14 | 1750 | 99.4 | 23 | 1.1 |
| 15 | 788 | 99.0 | 19 | 1.1 |
| 16 | 1023 | 99.2 | 17 | 1.1 |

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

The invention claimed is:

1. A method of automated preparation of an $^{18}$F-FACBC tracer composition within a cassette system comprising:
   (a) reacting in a reaction vessel of the cassette system a source of $^{18}$F-fluoride with a precursor compound of Formula I:

wherein:
LG is a leaving group;
$PG^1$ is a carboxy protecting group;
and, $PG^2$ is an amine protecting group;
to obtain a reaction mixture comprising a compound of Formula II:

wherein $PG^1$ and $PG^2$ are as defined for Formula I;
   (b) removing $PG^1$ to obtain a reaction mixture comprising a compound of Formula III:

wherein $PG^1$ is as defined for Formula I;
   (c) removing $PG^2$ to obtain a reaction mixture comprising anti-1-amino-3-$^{18}$F-fluorocyclobutyl-1-carboxylic acid ($^{18}$F-FACBC); and
   (d) purifying said reaction mixture comprising $^{18}$F-FACBC by passing it through only one solid phase extraction cartridge of the cassette system, wherein the solid phase extraction cartridge is a hydrophilic lipophilic balanced (HLB) solid phase extraction cartridge to obtain the $^{18}$F-FACBC tracer composition having greater than 99% radiochemical purity.

2. The method as defined in claim 1 wherein LG is trifluoromethanesulfonic acid.

3. The method as defined in claim 1 wherein $PG^1$ is ethyl.

4. The method as defined in claim 1 wherein $PG^2$ is t-butoxycarbonyl.

5. The method as defined in claim 1 wherein $PG^1$ is removed using NaOH.

6. The method as defined in claim 1 wherein $PG^2$ is removed using HCl.

7. The method as defined claim 1 further comprising formulating said purified reaction mixture obtained in step (d) with citrate buffer.

8. The method as defined in claim 1, wherein the resulting composition has an end of synthesis (EOS) radioactive concentration (RAC) of at least 1,000 MBq/mL, and comprises no more than 150 µg/mL hydroxyl-ACBC.

9. The method as defined in claim 1, wherein the purified reaction mixture as obtained in step (d) excludes breakthrough aluminum.

\* \* \* \* \*